US00PP36736P2

(12) United States Plant Patent
LaBonte et al.

(10) Patent No.: US PP36,736 P2
(45) Date of Patent: Jun. 10, 2025

(54) SWEETPOTATO PLANT NAMED 'LA18-100'

(50) Latin Name: ***Ipomoea batatas* (L.) Lam.**
Varietal Denomination: LA18-100

(71) Applicant: Board of Supervisors of Louisiana State University and Agricultural and Mechanical College, Baton Rouge, LA (US)

(72) Inventors: Don R. LaBonte, Baton Rouge, LA (US); Arthur Q. Villordon, Chase, LA (US); Tara P. Smith, Chase, LA (US); Jeffrey Cole Gregorie, Chase, LA (US); Imana Power, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 18/657,853

(22) Filed: May 8, 2024

(51) Int. Cl.
*A01H 5/06* (2018.01)
*A01H 6/00* (2018.01)

(52) U.S. Cl.
USPC ..... Plt./258
CPC ..... *A01H 6/00* (2018.05)

(58) Field of Classification Search
USPC ..... Plt./258
CPC ..... A01H 5/06
See application file for complete search history.

(56) References Cited

U.S. PATENT DOCUMENTS

| | | | | |
|---|---|---|---|---|
| PP19,955 | P2 | 4/2009 | LaBonte et al. | Plt./258 |
| PP22,719 | P3 | 4/2012 | LaBonte et al. | Plt./258 |
| PP23,761 | P3 | 7/2013 | LaBonte et al. | Plt./258 |
| PP23,785 | P3 | 7/2013 | LaBonte et al. | Plt./258 |
| PP25,308 | P3 | 2/2015 | LaBonte et al. | Plt./258 |
| PP26,735 | P3 | 5/2016 | LaBonte et al. | Plt./258 |
| PP32,021 | P2 | 7/2020 | LaBonte et al. | Plt./258 |

OTHER PUBLICATIONS https://journals.ashs.org/hortsci/view/journals/hortsci/59/6/article-p796.xml; May 3, 2024; 5 pages.*
LSU SweetPotato Research Station Invoices; Jan. 25, 2024, Feb. 5, 2024, Mar. 5, 2024, Mar. 7, 2024, Mar. 15, 2024, Mar. 18, 2024, Mar. 19, 2024, Mar. 22, 2024, and Mar. 27, 2024; 10 pages.*
2022 Summer Issue Louisiana Sweet Potato News p. 2.
2023 Summer Issue Louisiana Sweet Potato News p. 4.
2024 Summer Issue Louisiana Sweet Potato News pp. 1 to 3.
LSU Sweet Potato Research Station Invoices Jan.-Mar. 2024.
Avoyelles LA18-100 Release Presentation Mar. 2024.

* cited by examiner

*Primary Examiner* — Kent L Bell
(74) *Attorney, Agent, or Firm* — John H. Runnels

(57) ABSTRACT

A new variety of sweetpotato, identified as 'LA18-100,' is disclosed having resistance to both southern root-knot nematode and *Streptomyces* soil rot; an orange-fleshed storage root, copper to light rose skin, early crops, and high yields.

3 Drawing Sheets

Genus and species name: *Ipomoea batatas* (L.) Lam.
Variety denomination: 'LA18-100'.

BACKGROUND OF THE INVENTION

Sweetpotatoes (*Ipomoea batatas*), unlike Irish potatoes (*Solanum tuberosum*), are not tuber-propagated plants. A "tuber" is a short, thickened portion of an underground branch. Along a tuber are found "eyes," each of which comprises a ridge bearing a scale-like leaf (analogous to a branch leaf) having minute meristematic buds in the axial of the leaf. By contrast, sweetpotato roots are developmentally and anatomically true roots, lacking meristematic buds, and are not derived from an underground branch. Sweetpotatoes do not form tubers. Historically, producers have often run out of sweetpotato roots late in the storage season, and the quality of a 10-month-old stored sweetpotato can be inferior to that of a newly harvested crop. Producers sometimes harvest an undersized crop early in the production season to fill orders.

SUMMARY OF THE INVENTION

This invention pertains to a new and distinct variety of sweetpotato, *Ipomoea batatas* (L.) Lam. This new variety demonstrates superior resistance to southern root-knot nematode. Its storage root has orange flesh. It has an earlier date to harvest as compared to '05-111'. The novel variety represents an opportunity to supply retail and processors with an early crop before other crops have been harvested, with less loss of tonnage. It presents an opportunity to begin harvest several weeks in advance of the main crop. The new variety thus extends grower capacity to increase acreage, without necessarily increasing equipment resources. Irrigation can help optimize yields for early harvest. Yield and shape quality have been very good, even in poor growing environments. Storage is good; roots are sound and marketable after 6-8 months in storage; some late pithiness has been noted if the crop was grown under conditions of water stress. When cooked, 'LA18-100' has an excellent flavor.

The new and distinct sweetpotato variety has been named 'LA18-100'. The same variety is also known as 'Avoyelles'. It is characterized by a storage root with orange flesh, consistent shape, and high yield. 'LA 18-100' has an orange-fleshed, light rose- to copper-skinned sweetpotato root. The skin is lighter than that of 'Beauregard' (unpatented) or 'Orleans' (also known as experimental line 05-111, U.S. Plant Pat. No. 23,761) and is mostly smooth; lobing has been observed in a few environments. The flesh is uniformly deep orange and a bright color once baked. It is acceptable as a frozen fry product. 'LA 18-100' can be harvested just 90-100 days after planting, which is early. It has a superior yield for the U.S. #1 grade. It is highly resistant to southern root-knot nematode, *Meloidogyne incognita*. The variety's roots exhibit a consistent shape across the silt-loam soils of the Gulf South and the sandy soils of North and South Carolina. Growers' observations reported excellent transplant survival under hot and dry conditions. 'LA 18-100' is well-suited for the production environment in the Gulf South, and its quality is excellent in North and South Carolina production regions. Performance in California has not yet been tested.

DETAILED BOTANICAL DESCRIPTION

This new variety of sweetpotato, named 'LA18-100', resulted from an open-pollination cross performed in 2017 with the patented female parent '07-146' U.S. Plant Pat. No. 23,785. The male parent is unknown. Six patented male parents were among the potential pollen sources in the crossing nursery in Chase, Louisiana (along with other potential pollen sources besides these six): '05-111' U.S. Plant Pat. No. 23,761; 'LA13-81' U.S. Plant Pat. No. 32,021; 'LA06-52' U.S. Plant Pat. No. 26,735; 'Bonita' U.S. Plant Pat. No. 22,719; 'LA04-175' U.S. Plant Pat. No. 25,308; and 'Murasaki-29' U.S. Plant Pat. No. 19,955. 'LA18-100' was developed and selected to provide a variety with many characteristics similar to those of '05-111', but with an earlier date to harvest, and with resistance to southern root-knot nematode. The female parent '07-146' has some tricuspid leaves and red purple hues in the abaxial veins [2.5 Red (red) P (Purple) 4/4]. By contrast, 'LA18-100' does not have red purple hues in the abaxial veins, and has minor cusps along the leaf margin. Color terminology used throughout this specification is in accordance with the MUNSELL® Book of Color (2003 Edition, Munsell Color, GretagMacbeth LLC, 617 Little Britain Road, New Windsor, New York 12553-6148). The color descriptions and color illustrations are as nearly true as is reasonably possible. However, it is understood that both color and other phenotypic expressions described herein may vary from plant to plant with differences in growth, environment, and cultural conditions, without any change in the genotype of the variety 'LA18-100'.

There are other distinctions between the two varieties 'LA18-100' and '05-111.' 'LA18-100' has no red hue at the leaf petiole junction; while '05-111' has a red purple marking [5 R (red) P (Purple) (4/6)]. Roots of 'LA18-100' are a light copper to light rose, compared to the light-to-medium red of the roots of female parent '07-146'.

'LA18-100' roots were stored during the winter in Chase, LA. 'LA18-100' roots were planted the following spring, resulting in approximately 8-10 sprouts per root. Cuttings from the sprouts were successfully transplanted for asexual reproduction in Chase, LA. Asexual propagation of the new cultivar by cuttings has shown that the unique features of this new sweetpotato variety are stable, and that the plant reproduces true to type in successive generations of asexual propagation. Plants described herein were 90 days from planting in full-sun field plantings, unless otherwise noted.

Figure 1:
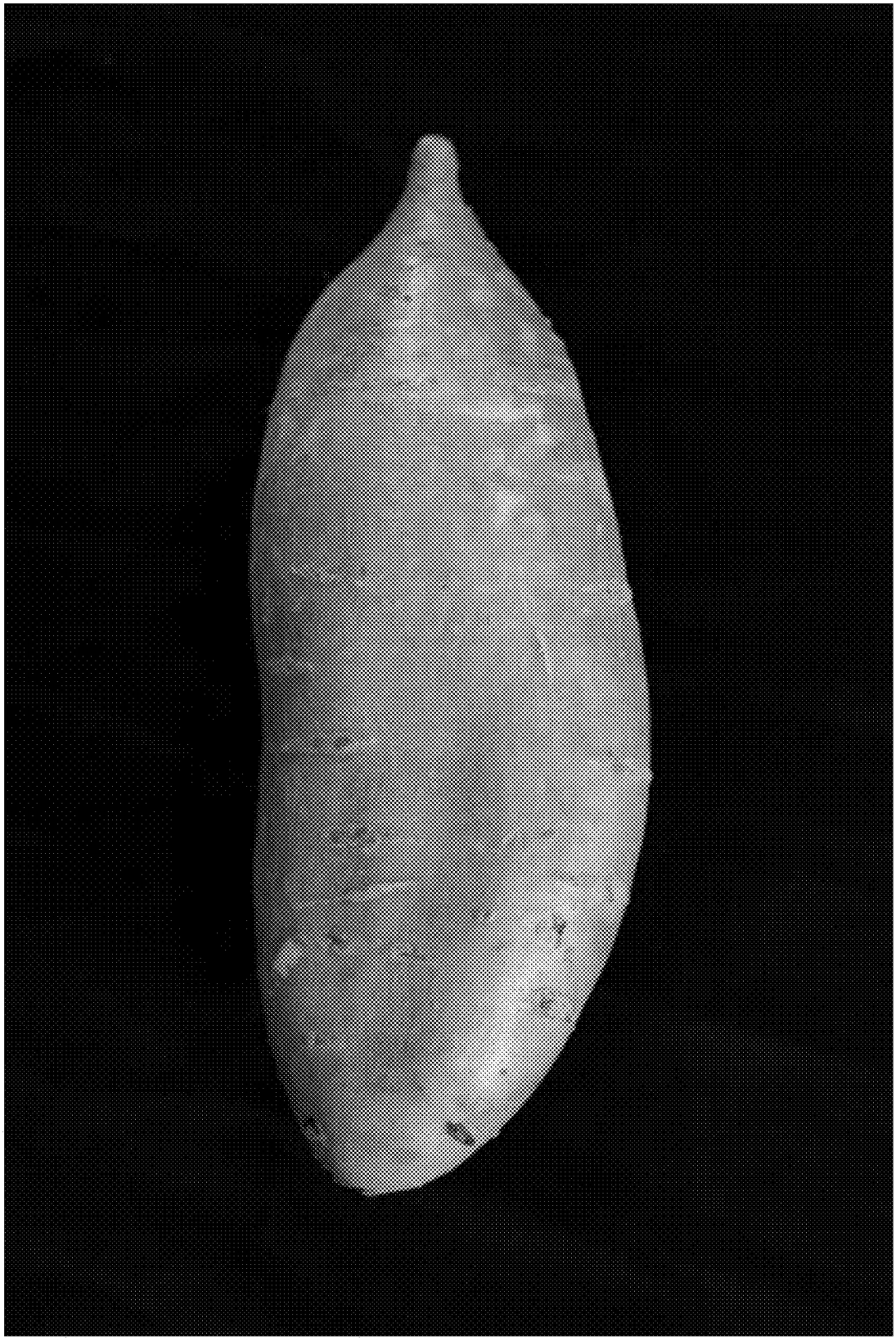
FIG. 1 is a color photograph of the mature, harvested fleshy root form of the novel variety of sweetpotato identified as 'LA18-100'.
Figure 2:
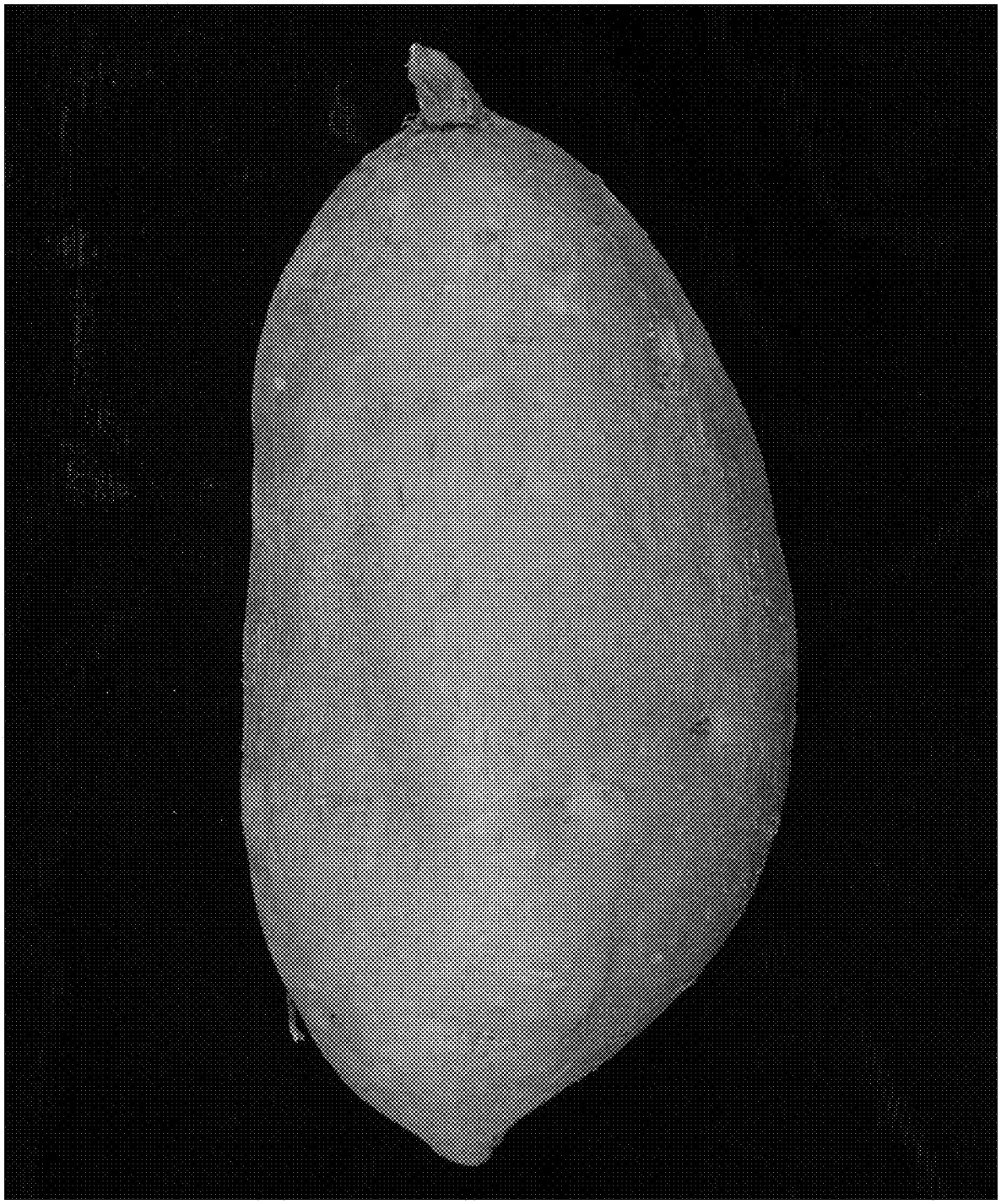
FIG. 2 is a color photograph of the mature, harvested fleshy root form of the sweetpotato variety identified as '05-111'.

FIG. 1 depicts the fleshy root form of the 'LA18-100' sweetpotato. The skin has a lighter color value (MUNSELL® Book of Color) from the light-to-medium rose of '05-111', both at harvest and after several months of storage, as summarized in Table 1. No eyes or longitudinal grooving was present. MUNSELL® Book of Color values and chroma for skin and flesh for both 'LA18-100' and '05-111' storage roots are shown in Table 1. The '05-111' sweetpotato is depicted for comparison in FIG. 2. The skins of both 'LA18-100' and '05-111' were smooth. The 'LA18-100' cortex was 3.7 mm in depth, and the color similar throughout. The flesh of 'LA18-100' was similar to that of '05-111'.

TABLE 1

| Characteristic | Variety | Color |
|---|---|---|
| Skin | 'LA18-100' | 5 Y (yellow) R (red) 7/6 |
| | '05-111' | 5 Y (yellow) R (red) 6/6 |
| Flesh | 'LA18-100' | 2.5 Y (yellow) R (red) 7/10 |
| | '05-111' | 2.5 Y (yellow) R (red) 7/8 |

Figure 3:
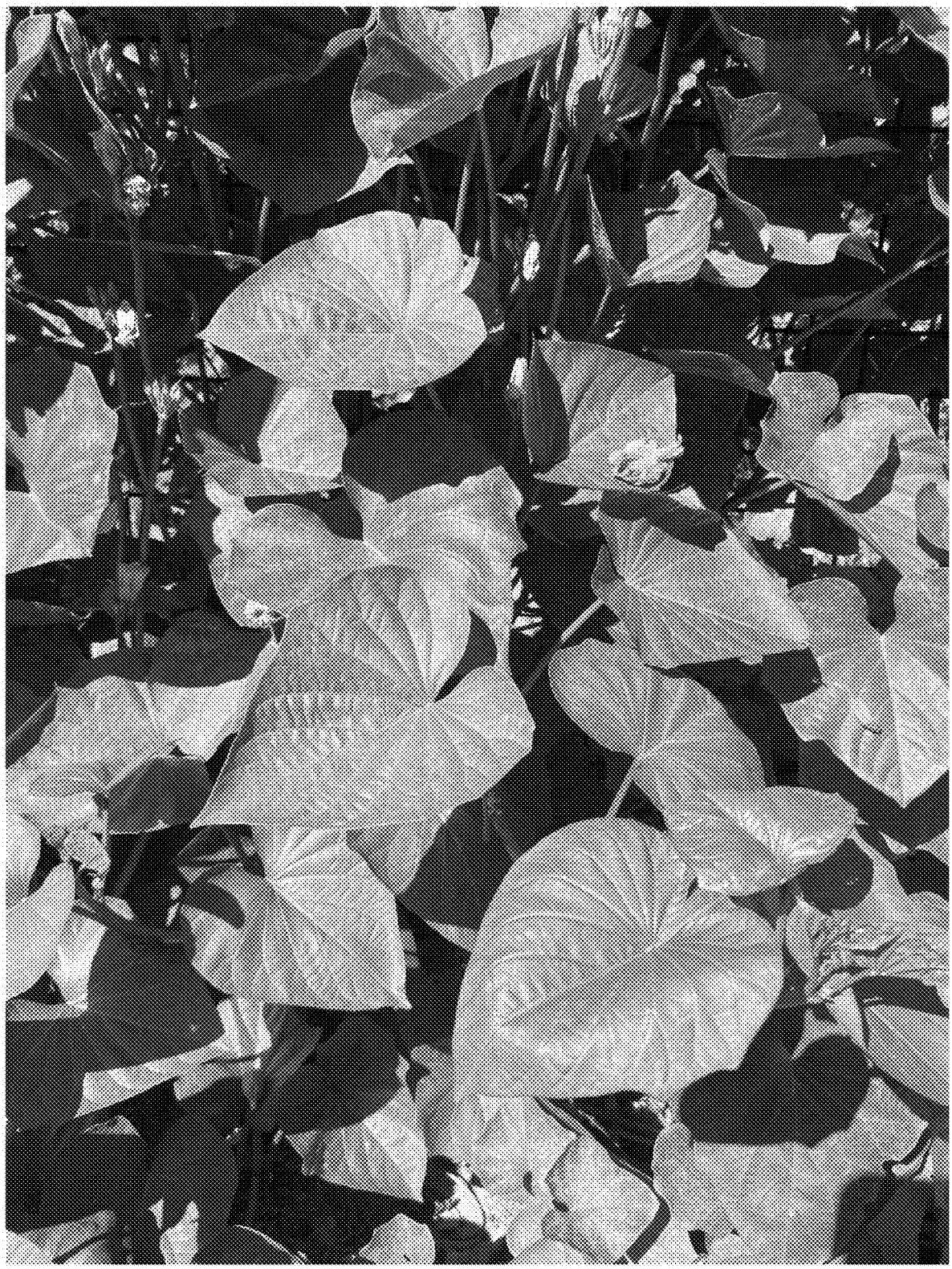
FIG. 3 is a color photograph of the mature canopy biomass of the novel variety of sweetpotato identified as 'LA18-100'.

FIG. 3 depicts the canopy biomass of the 'LA18-100' sweetpotato. Stems of 'LA18-100' are green and that color remains largely unchanged from the apex to the crown of the roots [2.5 G (green) Y (yellow) (5/6)]. The 'LA18-100' canopy biomass was similar to that of '05-111'. The 'LA18-100' canopy architecture was spreading, and averaged 20-25 cm in height from the soil surface, a height that is comparable to that of '05-111'. For 'LA18-100', three to four vines typically arose from the main stem near the soil surface. The main stem was typically 1.6-2 cm in diameter. Those 3-4 vines were typically about 140 cm in length, with diameters about 0.9 cm measured 65 cm from the base, and a diameter about 0.4-0.5 cm at the first internode of the first fully developed leaf from the apex. The spread was comparable to that of '05-111.' Six lateral branches typically arose from each of the main vines. At the first internode from the apex, the typical internode length was about 5.5 cm between the first and second fully developed leaves. Internode lengths for other sections of the vine averaged about 4.0 cm. Unfolded immature leaves were green [5 G (green) Y (yellow) (4/4)] on the adaxial and abaxial surfaces, which changed nominally over one to two nodes from the apex for the adaxial surface to a slightly darker green upper surface [5 G (green) Y (yellow) (3/4)]. The abaxial surface is lighter green [5 G (green) Y (yellow) (4/4)]. Anthocyanin pigmentation and pubescence were both absent. Mature leaves at five nodes from the apex had an acute apex and mostly a cordate base with an entire leaf margin. Some leaves had one to three small cusps (projecting 3 mm) on each side of the lamina. Mature leaves were about 13 cm long and 11 cm wide. Adaxial and abaxial veins had a pinnate venation pattern, with no coloration change from the lamina surface.

Abaxial and adaxial surfaces were slightly puckered between veins. The petiole was green [5 G (green) Y (yellow) (3/4)], transitioning towards the base of the stem to a lighter green matching the stem coloration [2.5 G (green) Y (yellow) (5/6)]. No change in color occurred at the base of the leaf junction with the petiole. The petiole was typically 10 cm long at five nodes from the apex, and 2.5 mm in diameter at 5 cm from the leaf junction. The dormant nodal meristem had no change in color [2.5 G (green) Y (yellow) (5/6)] from the stem.

A typical inflorescence of 'LA18-100' comprised one cluster of five-seven flowers per peduncle. Peduncles were green [2.5 G (green) Y (yellow) (5/6)], about 10 cm long, and about 3 mm in diameter. Individual flowers were about 2.7 cm long from the base of the calyx, and the corolla was 2.6-3 cm wide at the opening. The fused flower petals formed a pentagonal pattern with smooth edges. The inner throat of the corolla was purple [7.5 R (red) P (purple) (2/6)]. The inner and outer limbs of the corolla (the corolla's outermost area, distal from the calyx) were light purple [10 P (purple) (5/6)]. The five sepals comprising the calyx were elliptical with a cordate apex, and were green [2.5 G (green) Y (yellow) (6/6)]; three of these sepals were about 11 mm long and 5.6 mm wide. Two other sepals (interspersed) were about 8 mm long and 3 mm wide. Sepal margins were entire. Stigmata were about 1.3 cm long and light purple [2.5R (red) P (purple) (5/6)] at the base, fading towards the stigma. Five stamens were inferior to the stigmata. A slight fragrance was present. Mature seed capsules were round and 6.0 mm in length and width, and the seeds were 3.5 mm and round. One black [neutral 1.75] seed was produced on average per capsule.

EXAMPLE 1

Tests Conducted

To confirm the novelty of 'LA18-100' as a variety, controlled tests (e.g., pathogen responses and yield) were conducted in Baton Rouge, Louisiana. The cultivar '05-111' was selected for comparison because of its importance in commercial United States orange-flesh sweetpotato acreage. Diseases that commonly affect the growth of sweetpotatoes were selected to test for pathogen responses in both varieties. 'LA18-100' and '05-111' were both intermediate-to-resistant for *Streptomyces* soil rot caused by *Streptomyces ipomoeae* (Person & W. J. Martin) Waksman & Henrici. 'LA18-100' was susceptible-to-intermediate, and '05-111' was resistant to *Fusarium* wilt or stem rot caused by *Fusarium oxysporum* Schlect. f. sp. *batatas* (Wollenw.) Snyd. & Hans. 'LA18-100' was intermediate-to-susceptible, while '05-111' was resistant to *Rhizopus* soft rot caused by *Rhizopus stolonifer* (Ehr. ex. Fr.) Lind. 'LA18-100' and '05-111' were both susceptible to bacterial root rot caused by *Dickeya dadantii* Samson et al. as measured by postharvest inoculation of storage roots.

Susceptibility to nematodes was measured in greenhouse tests. 'LA18-100' was very resistant, while '05-111' was very susceptible to race 3 of the southern root-knot nematode, *Meloidogyne incognita* (Kofoid & White 1919) Chitwood 1949.

'LA18-100' and '05-111' are both drought- and heat-tolerant, and both die under freezing temperatures.

'LA18-100' did not exhibit any novel insect resistance. 'LA18-100' and '05-111' both showed similar susceptibility to the banded cucumber beetle (*Diabrotica balteata* LeConte) in 2021 and 2022 trials.

To determine yield, complete-block trials with three or four replicates of 'LA18-100' and '05-111' each were conducted in 2022 and 2023 in areas of Louisiana, Mississippi, Arkansas, and South Carolina considered likely to grow 'LA18-100.' 'LA18-100' and '05-111' sweetpotato plants were transplanted in randomized complete-block trials at 31 cm spacings. Each block/plot was fertilized with approximately 250 pounds per acre of a mixed fertilizer comprising 13% N, 13% $P_2O_5$, and 13% $K_2O$. 'LA18-100' was compared to '05-111' at transplanting dates in May-June. Average yields were measured for each of the following grades of roots: U.S. #1 (51-89 mm in diameter, 76-229 mm long); Canner (25-51 mm in diameter, 51-178 mm long); and Jumbo (larger than U.S. #1 in diameter, length, or both, and without objectionable defects). A typical marketable root of 'LA18-100' was 160-180 mm long, 65-75 mm in diameter, with a mostly elliptic shape. The base or distal end tended to be more elongated in comparison to a slightly rounder apex (proximal end). U.S. #1 roots typically weighed 150-190 g.

An early-season transplanting date trial was conducted at Senatobia, Mississippi in 2022. 'LA18-100 and '05-111' were transplanted on May 31, 2022 and harvested on Oct. 13, 2022 (136 days after planting). Average yields, measured as Metric Tons per Hectare (MT/ha), for 'LA18-100' and '05-111' are shown in Table 2.

TABLE 2

Early-season transplant date yield trial.

| Selection | US#1† | Canners† | Jumbos† | TMY‡† |
|---|---|---|---|---|
| 'LA8-100' | 47.1a | 18.7a | 8.3a | 74.0a |
| '05-111' | 30.4b | 18.7a | 5.3a | 54.3a |

†Average yields in MT/ha of varieties. Figures within the same column that are followed by a common letter do not differ significantly ($P < 0.05$) according to Duncan's Multiple Range Test.
TMY‡ = total marketable yield A mid-season transplanting date trial was also conducted at Ville Platte, Louisiana in 2022. 'LA18-100' and '05-111' were transplanted on Jun. 7, 2022 and harvested on Oct. 24, 2022 (140 days after planting). Average yields, measured as Metric Tons per Hectare (MT/ha), for 'LA18-100' and '05-111' are shown in Table 3.

TABLE 3

Mid-season transplant date yield trial.

| Selection | US#1† | Canners† | Jumbos† | TMY‡† |
|---|---|---|---|---|
| 'LA8-100' | 26.7a | 6.6a | 6.4a | 39.7a |
| '05-111' | 14.6a | 9.5a | 1.3a | 25.4b |

†Average yields in MT/ha of varieties. Figures within the same column that are followed by a common letter do not differ significantly ($P < 0.05$) according to Duncan's Multiple Range Test.
TMY‡ = total marketable yield A mid-season transplanting date trial was also conducted at Windsor, South Carolina in 2022. 'LA18-100' and '05-111' were transplanted on Jun. 14, 2022 and harvested on Nov. 8, 2022 (147 days after planting). Average yields, measured as Metric Tons per Hectare (MT/ha), for 'LA18-100' and '05-111' are shown in Table 4.

TABLE 4

Mid-season transplant date yield trial.

| Selection | US#1† | Canners† | Jumbos† | TMY‡† |
|---|---|---|---|---|
| 'LA8-100' | 45.8a | 16.5a | 21.5a | 83.8a |
| '05-111' | 32.9a | 10.4a | 3.4b | 46.6b |

†Average yields in MT/ha of varieties. Figures within the same column that are followed by a common letter do not differ significantly ($P < 0.05$) according to Duncan's Multiple Range Test.
TMY‡ = total marketable yield A mid-season transplanting date trial was also conducted at Delhi, Louisiana in 2023. 'LA18-100' and '05-111' were transplanted on Jun. 13, 2023 and harvested on Oct. 24, 2023 (133 days after planting). Average yields, measured as Metric Tons per Hectare (MT/ha), for 'LA18-100' and '05-111' are shown in Table 5.

TABLE 5

Mid-season transplant date yield trial.

| Selection | US#1† | Canners† | Jumbos† | TMY‡† |
|---|---|---|---|---|
| 'LA8-100' | 32.9a | 10.5a | 14.3a | 57.5a |
| '05-111' | 17.9b | 10.3a | 2.7a | 31.0b |

†Average yields in MT/ha of varieties. Figures within the same column that are followed by a common letter do not differ significantly ($P < 0.05$) according to Duncan's Multiple Range Test.
TMY‡ = total marketable yield A mid-season transplanting date trial was also conducted at Belzoni, Mississippi in 2023. 'LA18-100' and '05-111' were transplanted on Jun. 6, 2023 and harvested on Sep. 7, 2023 (93 days after planting). Average yields, measured as Metric Tons per Hectare (MT/ha), for 'LA18-100' and '05-111' are shown in Table 6.

TABLE 6

Mid-season transplant date yield trial.

| Selection | US#1† | Canners† | Jumbos† | TMY‡† |
|---|---|---|---|---|
| 'LA8-100' | 30.2a | 17.5a | 15.9a | 63.7a |
| '05-111' | 11.8b | 8.11b | 0.4b | 22.2b |

†Average yields in MT/ha of varieties. Figures within the same column that are followed by a common letter do not differ significantly ($P < 0.05$) according to Duncan's Multiple Range Test.
TMY‡ = total marketable yield As seen in Tables 2-6, 'LA18-100' produced yields that were at least comparable to, and were often superior to those of '05-111' in regional trials on various planting dates. Yields in heavier silt loam soil (Tables 3 and 5) were similar to those in lighter, sandy loam soils (Tables 2, 4, and 6). Replicated plots at other farms and on the research station showed fairly consistent yields for 'LA18-100' with early, middle, or late season plantings (data not shown). Yield declines in poor growing environments were within expected norms. 'LA18-100' typically produced harvestable roots approximately 93-120 days after planting, which is early for sweetpotatoes generally, and is early in comparison to '05-111'. The Jumbo grade yield was indicative of earliness. 'LA18-100' had a higher jumbo yield in comparison to '05-111'. Overall, the data reflected consistently high yields for 'LA18-100'. 'LA18-100' has been observed to have a storage life and shipping quality comparable to those for '05-111'.

Observations on 'LA18-100' Disease Resistance Profile
Fusarium wilt—susceptible to intermediate
Southern root-knot nematode—highly resistant
Guava root-knot nematode—susceptible
Bacterial soft rot—susceptible
Soil rot—intermediate to resistant
Rhizopus soft rot—susceptible to intermediate Observations on 'LA18-100' Insect Resistance. 'LA18-100' showed similar banded cucumber beetle damage (*Diabrotica balteata* LeConte) in comparison to 'Orleans' in 2021 and 2022 replicated trials at Alexandria, Louisiana. There was similar damage from the sweet potato weevil, *Cylas formicarius elegantulus* (Summers), in comparison to 'Orleans', and greater damage (percentage of injured roots) in comparison to 'Murasaki-29', a resistant check variety. 'LA18-100' has not demonstrated any unusual propensity for insect damage in numerous on-farm trials in the Gulf South.

'LA18-100' roots stored for three months in 2023-24 were characterized for nutritional content by an independent laboratory. The analyzed sample comprised three randomly-selected roots. Total carbohydrates were 18.1 g per 100 g on a fresh weight basis (fwb). Dietary fiber was 2.53 g per 100 g fwb. Calcium was 35.2 mg per 100 g fwb, which represents ~4% of recommended daily dietary requirements in a 110 g serving. Vitamin C was 8.94 mg per 100 g fwb, which represents ~10% of recommended daily dietary requirements in a 110 g serving. Potassium was 350 mg per 100 g fwb, which represents ~8% of recommended daily dietary requirements in a 110 g serving. Total vitamin A in Retinol, Activity Equivalents (RAE) was 566 mcg RAE per 100 g fwb, which represents ~70% of recommended daily dietary requirements in a 110 g serving. Dry matter content was 20.6%.

Miscellaneous Observations:

1. S-metolachlor herbicide—Anecdotal observations from plots treated prior to or just after planting found some damage (mis-shaped roots) to a greater extent than for the varieties 'Beauregard' or 'Orleans'. It is recommended for now to apply S-metolachlor 7-10 days post planting, which is the normal recommended interval after planting.
2. Root skin color can vary when harvested late in cold soils. Harvests in cold soils have shown patches of rose coloration. This variation in root skin color has not been noted when harvested in the prime harvest season.
3. Over-production of jumbo grade—'LA18-100' can transform fairly quickly from U.S. #1 grade to the less valuable jumbo grade, depending particularly on the timing of rainfall. The 'LA18-100' variety is therefore expected to be better suited for bulk processing production, where tonnage is important, than for the fresh market.
4. Irrigation has been found to optimize yield and reduce the number of growing days to harvest. 'LA18-100' nevertheless also performs well in poorer environments.
5. Some ribbing (longitudinal ridges along storage root) has been noted in later-harvested crops (120+ days after planting), as well as on jumbos. Ribbing may be greater after plants renew growth following rains that end an extended drought.
6. Anecdotal observations suggest that 'LA18-100' has excellent transplant survivability and stand under high temperature, dry conditions.
7. Storage roots intended for plant beds are preferably pre-sprouted for 7 days at 29° C. By contrast, storage roots that were bedded directly from 18° C. storage produced plants more sporadically and in smaller numbers.

8. There can be a tendency for growth cracks to appear on jumbo roots, particularly when plants renew growth after rainfall ends an extended drought.
9. 'LA18-100' is not expected to be a "universal" variety such as 'Bellevue' (also known as experimental line LA06-52, U.S. Plant Pat. No. 26,735); it is not expected to grow well in all soils and all environments.

'LA18-100' is a valuable new commercial sweetpotato variety. 'LA18-100' has yields that equal and often exceed yields for US #1 and total marketable yield in comparison to '05-111'. 'LA18-100' is resistant to southern root-knot nematode.

What is claimed is:

1. A new and distinct variety of *Ipomoea batatas* plant named 'LA18-100', as described and illustrated herein.

* * * * *